United States Patent
Blasco et al.

(10) Patent No.: US 8,460,989 B2
(45) Date of Patent: Jun. 11, 2013

(54) NIOBIUM AND VANADIUM ORGANOMETALLIC PRECURSORS FOR THIN FILM DEPOSITION

(75) Inventors: Nicolas Blasco, Grenoble (FR); Anthony Correia-Anacleto, Maisons-Alfort (FR); Audrey Pinchart, Antony (FR); Andreas Zauner, Voisins le Bretonneux (FR)

(73) Assignee: L'Air Liquide Societe Anonyme pour l'Etude et l'Exploitation des Procedes, Paris (FR)

( * ) Notice: Subject to any disclaimer, the term of this patent is extended or adjusted under 35 U.S.C. 154(b) by 0 days.

(21) Appl. No.: 13/123,013

(22) PCT Filed: Oct. 6, 2009

(86) PCT No.: PCT/EP2009/062964
§ 371 (c)(1),
(2), (4) Date: Apr. 7, 2011

(87) PCT Pub. No.: WO2010/040741
PCT Pub. Date: Apr. 15, 2010

(65) Prior Publication Data
US 2011/0195574 A1 Aug. 11, 2011

(30) Foreign Application Priority Data
Oct. 7, 2008 (EP) .................... 08305649

(51) Int. Cl.
H01L 21/8238 (2006.01)
H01L 21/4763 (2006.01)
C23C 16/00 (2006.01)
C07F 9/00 (2006.01)

(52) U.S. Cl.
USPC ...... 438/199; 438/643; 427/250; 427/255.28; 556/42

(58) Field of Classification Search
USPC ........ 438/199, 643; 427/250, 255.28; 556/42; 257/E21.002
See application file for complete search history.

(56) References Cited

U.S. PATENT DOCUMENTS

| | | | |
|---|---|---|---|
| 4,245,131 A * | 1/1981 | Schrock | 585/511 |
| 6,268,288 B1 | 7/2001 | Hautala et al. | |
| 6,368,398 B2 | 4/2002 | Vaartstra | |
| 6,491,978 B1 | 12/2002 | Kalyanam | |
| 6,503,561 B1 | 1/2003 | Senzaki et al. | |
| 6,593,484 B2 | 7/2003 | Yasuhara et al. | |
| 6,743,473 B1 | 6/2004 | Parkhe et al. | |
| 7,193,098 B1 | 3/2007 | Lucey et al. | |
| 7,348,445 B2 | 3/2008 | Peters et al. | |
| 2004/0219784 A1 | 11/2004 | Kang et al. | |
| 2007/0042213 A1* | 2/2007 | Reuter et al. | 428/620 |
| 2007/0218683 A1 | 9/2007 | Ishizaka et al. | |
| 2008/0050916 A1 | 2/2008 | Yonker et al. | |
| 2008/0081127 A1* | 4/2008 | Thompson et al. | 427/569 |
| 2008/0213999 A1 | 9/2008 | Wagner | |
| 2008/0248648 A1 | 10/2008 | Thompson et al. | |
| 2009/0311879 A1* | 12/2009 | Blasco et al. | 438/785 |
| 2010/0055310 A1* | 3/2010 | Merle et al. | 427/250 |

FOREIGN PATENT DOCUMENTS

| | | |
|---|---|---|
| EP | 1 884 517 | 2/2008 |
| EP | 1 884 518 | 2/2008 |
| EP | 2 065 390 | 6/2009 |
| JP | 2001 329367 | 11/2001 |
| KR | 10-2008-0119084 | * 11/2008 |
| WO | WO 02 20870 | 3/2002 |

OTHER PUBLICATIONS

Pairwise ligand exchange reactions in tetrahedral and pseudo-tetrahedral transistion metal complexes, Vernon C. Gibson, et al., Dalton Transactions, pp. 4457-4465, Royal Society of Chemistry, 2003.*
Niobium-n-cyclopentalenyl compounds with imido and amido ligands derived from 2,6-dimethylaniline, Martin J. Humphries, et al., J. Chem. Soc., Dalton Trans., pp. 4555-4562, Royal Society of Chemistry, 2000.*
Niobium-n-cyclopentadienyl compounds with imido and amido ligands derived from tert-butylamine, Martin J. Humphries, et al., J. Chem. Soc., Dalton Trans., pp. 4044-4051, Royal Society of Chemistry, 2000.*
Structure Dynamics in Novel ansa-Metallocenes of Niobium and Tantalum, Wolfgang A Herrmann, et al., Angew. Chem. Int. Ed. Engl., vol. 35, No. 17, pp. 1951-1953, 1996.*
Djakovitch, L. et al., "Bridged half-sandwich niobiocenes by intramolecular CH activation," Journal of Organometallic Chemistry, vol. 545-546, Oct. 30, 1997, pp. 399-405.

(Continued)

*Primary Examiner* — Kevin Parendo
(74) *Attorney, Agent, or Firm* — Patricia E. McQueeney

(57) ABSTRACT

Disclosed are methods for forming a metal-containing layer on a substrate. A vapor comprising at least one precursor compound selected from the group consisting of (Cp)V(=NtBu)(NEt$_2$)$_2$; (Cp)V(=NtBu)(NMe$_2$)$_2$; (Cp)V(=NtBu)(NEtMe)$_2$; (Cp)V(=NiPr)(NEt$_2$)$_2$; (Cp)V(=NiPr)(NMe$_2$)$_2$; (Cp)V(=NiPr)(NEtMe)$_2$; (Cp)V(=NC$_5$H$_{11}$)(NEt$_2$)$_2$; (Cp)V(=NC$_5$H$_{11}$)(NMe$_2$)$_2$; (Cp)V(=NC$_5$H$_{11}$)(NEtMe)$_2$; (Cp)Nb(=NtBu)(NEt$_2$)$_2$; (Cp)Nb(=NtBu)(NMe$_2$)$_2$; (Cp)Nb(=NtBu)(NEtMe)$_2$; (Cp)Nb(=NiPr)(NEt$_2$)$_2$; (Cp)Nb(=NiPr)(NMe$_2$)$_2$; (Cp)Nb(=NiPr)(NEtMe)$_2$; (Cp)Nb(=NC$_5$H$_{11}$)(NEt$_2$)$_2$; (Cp)Nb(=NC$_5$H$_{11}$)(NMe$_2$)$_2$; and (Cp)Nb(=NC$_5$H$_{11}$)(NEtMe)$_2$ is provided. At least one reaction gas selected from the group consisting of ozone and water is provided. The vapor and the reaction gas react with the substrate according to a deposition process to form the metal-containing layer on at least one surface of the substrate.

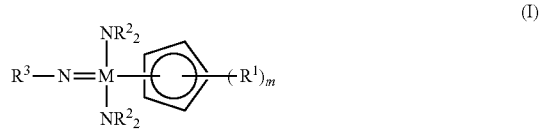

(I)

16 Claims, No Drawings

OTHER PUBLICATIONS

Djakovitch, L. et al., "Half-sandwich *ansa*—niobiocenes: synthesis and reactivity," Journal of Organometallic Chemistry, vol. 562, No. 1, Jul. 10, 1998, p. 71-78.

International Search Report for related PCT/EP2009/062964, Nov. 16, 2009.

EP Search Report for related EP 08 30 5649, Mar. 12, 2009.

Ahn, H. et al., "High-resolution solid-state 13C NMR studies of Chemisorbed organometallics, Chemisportive formation of cation-like and alkylidene organotantalum complexes on high surface area inorganic oxides, " Journal of the American Chemical Society, 124(24), 7103-7110, 2002.

Bitterwolf, T.E. et al., "Improved synthesis of $(\eta^5\text{-CpR})M(CO)_4$ compounds and the Nujol matrix photochemistry of $(\eta^5C_5H_5)M(CO)_4$ and $(\eta^5\text{-}C_9H_7)M(CO)_4$ where M=Nb and Ta, " Journal of Organometallic Chemistry 557 (1998), pp. 77-92.

Green, M.L. et al., "Chemical vapor depostion of metals for intergrated circuit applications, " Journal of Metals 37 (1985) 63.

Mayer, J.M. et al. "Hydrogen-transfer reaction which generate new imine, imido, and trimethylenemethane complexes of tantalum. " Journal of the American Chemical Society, 105(9), 2651-60, 1983.

Mayer, J.M. et al., "Synthesis and reactivity of new polyhydride compounds of tantalum(V), " Journal of the American Chemical Society, 104(8), 2157-65, 1982.

Wood, C.D. et al., "Reaction of CO with Ta(n5-C5Me5)Me4, Intramolecular reductive coupling of carbon monoxide via an 'n2-acetone' intermediate, " Journal of the American Chemical Society, 101(18), 1979, pp. 5421-5422.

Written Opinion for corresponding PCT/EP2009/062964, Nov. 16, 2009.

International Search Report and Written Opinion for related PCT/EP2007/061216, Jan. 15, 2008.

* cited by examiner

NIOBIUM AND VANADIUM ORGANOMETALLIC PRECURSORS FOR THIN FILM DEPOSITION

CROSS REFERENCE TO RELATED APPLICATIONS

This application is a 371 of International PCT Application PCT/EP2009/062964, filed Oct. 6, 2009, which claims priority to EP Application 08305649.9, filed Oct. 7, 2008, the entire contents of both are incorporated herein by reference.

SUMMARY

The invention relates to a new class of chemical compounds and their use in metal containing film deposition.

BACKGROUND

The continuous shrink of the critical sizes in modern Integrated Circuit (IC) features associated with 3D topology architectures offers highest density at the expense of process complexity.

According to the International Technology Roadmap for Semiconductors (ITRS), physical techniques commonly used in the semiconductor industry for the deposition of thin films are no more suitable to meet the requirements in the future technology node, notably for high aspect ratio structures. Techniques like PVD (Physical Vapor Deposition), i-PVD (ionized-Physical Vapor Deposition) or PECVD (Plasma-Enhanced Chemical Vapor Deposition), employing high energy particles, induce high sticking coefficient which leads to poor step coverage, especially along the sidewalls.

The main industrial options to enable the deposition of highly uniform and conformal thin films with reasonable throughput in high aspect ratio structures are techniques such as MOCVD (Metal-Organic Chemical Vapor Deposition) or ALD (Atomic Layer Deposition).

However, films deposited by MOCVD need high thermal budget and generally follow a 3D-growth mechanism described by a Volmer-Weber model. Thin films grow by clusters nucleation and such technique leads to insufficient step coverage.

The typical ALD process (e.g as described in RITALA M., LESKELA M., Atomic Layer Deposition, Handbook of thin films materials) involves gaseous reactants led onto a substrate by pulses, separated by inert gas purging. In MOCVD, gaseous reactants are injected simultaneously and react by thermal self-decomposition while in ALD; the loss of the ligand is thermally induced by reaction with the surface groups on the substrate. In a temperature range, the surface reactions are self-limited, which allow the deposition of highly uniform and conformal films. Precursors must be volatile and stable enough to be easily transferred to the reaction chamber without being decomposed.

Moreover, they must be reactive enough with the chemical groups of the surface to ensure reasonable growth rate.

ALD is of particular interest for the deposition of group V (V, Nb, Ta) metal containing films. Today, there still exist the needs for metal organic precursors in liquid state at room temperature (or close to room temperature) having a high volatility and having a high versatility: suitable for various applications in the semi-conductor manufacture. Interest for conductive (resistivity <1000 µΩ.cm) group V (V, Nb, Ta) metal containing thin films deposited by ALD has risen in the past few years for several main applications such as: copper diffusion barrier in BEOL applications, CMOS metal gate, electrodes for Metal-Insulator-Metal applications (DRAM . . . ), and/or the like in TFT-LCD applications.

Group V (V, Nb, Ta) metal containing films are also of particular interest for High-k layers in memory devices Halides such as $CpNbCl_4$ (CAS 33114-1507), $NbF_5$, $NbBr_5$ (Thin solid films, 1981, 79, 75), $NbCl_5$ (Crystal growth, 1978, 45, 37) and such as $TaCl_5$, disclosed in U.S. Pat. No. 6,268,288, have been widely investigated. However, some by-products generated during the deposition process, such as HCl or $Cl_2$, can cause surface/interface roughness that can be detrimental to the final properties. Moreover, Cl or F impurities can be detrimental to the final electrical properties. It is therefore expected to find new compounds having sufficient volatility but without containing Cl, F, or Br atoms.

Many Group V precursors have been considered to enable such deposition. Examples can be given as follows:

Alkoxides such as penta-ethoxy-Tantalum (PET) are widely used and described. However, they lead to oxygen containing films and are not suitable for the deposition of metal containing films which are used in particular as electrodes and which should not contain oxygen even at trace level. The same problem is observed for compounds such as $Cp_2Nb(H)(CO)$, $CpNb(CO)_4$ (J. Organomet. Chem 557 (1998) 77-92), $V(CO)_6$ (Thermochimica Acta, 1984, 75, 71), $(\eta^5-C_5H_5)V(CO)_4$ (M. L. Green, R. A. Levy, J. Metals 37 (1985) 63).

U.S. Pat. No. 6,379,748 discloses an improvement to PET. Alkyl bonds have been introduced, e.g. by using $TaMe_3(OEt)_2$ instead of $Ta(OEt)_5$ (PET). Volatility was thereby significantly improved without affecting the melting point.

However, $TaMe_3(OEt)_2$ does not allow versatile deposition: in particular, oxygen free metal cannot be obtained.

U.S. Pat. No. 6,368,398 discloses another improvement with the use for instance of $Ta[OC(O)C(CH_3)_3]_5$, however with the same limitation as disclosed here above.

WO 02/20870 discloses the use of tert-butylimido(tris(diethylamido)Tantalum, TBTDET, for the deposition of $Ta_2O_5$.

U.S. Pat. No. 6,593,484, US 2004/0219784 disclose a method of deposition of Tantalum nitride films by sequential injection of TBTDET or TAIMATA and other N source.

U.S. Pat. No. 6,379,748 discloses $Ta(Me_3SiCp)_2H_3$, which is a biscyclopentadienyl Ta hydride which is a solid having a low volatility.

DESCRIPTION OF PREFERRED EMBODIMENTS

The invention includes both methods and compounds to achieve the desired results, as described, but is not limited to the various embodiments disclosed.

According to a first embodiment, the invention relates to a compound of the formula $Cp(R^1)_mM(NR^2_2)_2(=NR^3)$ (I):

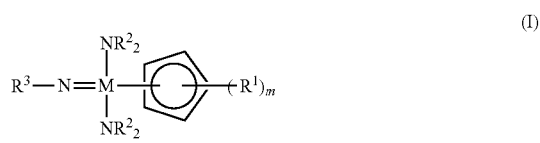

Wherein:

M is a metal independently selected from Vanadium (V) or Niobium (Nb) and m≤5;

$R^1$ is an organic ligand, each one independently selected in the group consisting of H, linear or branched hydrocarbyl radical comprising from 1 to 6 carbon atom;

$R^2$ is an organic ligand, each one independently selected in the group consisting of H, linear or branched hydrocarbyl radical comprising from 1 to 6 carbon atom;

$R^3$ is an organic ligand selected in the group consisting of H, linear or branched hydrocarbyl radical comprising from 1 to 6 carbon atom.

Alternatively, $R^1$ is an organic ligand, each one independently selected in the group consisting of H, linear or branched; alkyl, alkylsilyl, alkylamides, alkylsilylamides and/or alkoxides. $R^2$ may be chosen between an alkyl, alkylsilyl, alkylamides, alkylsilylamides and/or alkoxides. $R^3$ may be chosen between an alkyl, alkylsilyl, alkylamides, alkylsilylamides and/or alkoxides, preferably, $R^3$ is an alkyl with 3 or 4 carbon atoms such as isopropyl or tert-butyl.

In a specific configuration, each $R^1$ and $R^2$ is different from one another, which can have beneficial features on the compound physical properties.

Alternatively, $R^1$ is selected in the group consisting of H, an alkyl comprising from 1 to 4 carbon atom, preferably, $R^1$ is H or methyl or ethyl or isopropyl or tert-butyl;

$R^2$ is an alkyl comprising from 1 to 3 carbon atom, more preferably, $R^2$ is an alkyl with 1 or 2 carbon atom; and $R^3$ is alkyl with 3 or 4 carbon atoms; more preferably, $R^3$ is isopropyl or tert-butyl.

According to other embodiments, the invention relates to:

A compound, wherein each $R^1$ are different from one another and each $R^2$ are different from one another.

A compound, wherein m=0 in the formula (I).

The compounds:

(Cp)V(=NtBu)(NEt$_2$)$_2$
(Cp)V(=NtBu)(NMe$_2$)$_2$
(Cp)V(=NtBu)(N(EtMe)$_2$
(Cp)V(=NiPr)(NEt$_2$)$_2$
(Cp)V(=NiPr)(NMe$_2$)$_2$
(Cp)V(=NiPr)(NEtMe)$_2$
(Cp)V(=NC$_5$H$_{11}$)(NEt$_2$)$_2$
(Cp)V(=NC$_5$H$_{11}$)(NMe$_2$)$_2$
(Cp)V(=NC$_5$H$_{11}$)(NEtMe)$_2$
(Cp)Nb(=NtBu)(NEt$_2$)$_2$
(Cp)Nb(=NtBu)(NMe$_2$)$_2$
(Cp)Nb(=NtBu)(N(EtMe)$_2$
(Cp)Nb(=NiPr)(NEt$_2$)$_2$
(Cp)Nb(=NiPr)(NMe$_2$)$_2$
(Cp)Nb(=NiPr)(NEtMe)$_2$
(Cp)Nb(=NC$_5$H$_{11}$)(NEt$_2$)$_2$
(Cp)Nb(=NC$_5$H$_{11}$)(NMe$_2$)$_2$
(Cp)Nb(=NC$_5$H$_{11}$)(NEtMe)$_2$

According to another embodiment, the invention relates to a method for forming a metal-containing layer on a substrate, the method comprising at least the steps of:

a) providing a vapor comprising at least one precursor compound of the formula (I);

b) reacting the vapor comprising the at least one compound of formula (I) with the substrate, according to a deposition process, to form a layer of a metal-containing complex on at least one surface of said substrate.

According to other embodiments, the invention relates to:

A method, wherein the said deposition process is an atomic layer deposition process.

A method, wherein the said deposition process is a chemical vapor deposition process.

A method, further comprising the step:

c) reaction of the complex obtained in step b) with a reagent selected from another metal source, reducing reactants and/or nitriding reactants and/or oxidizing reactants.

A method, wherein the vapour provided in step a) further comprises one or more metal (M')-organic precursor(s) to produce thin films containing M and M'.

A method, further comprising providing at least one reaction gas wherein the at least one reaction gas is selected from the group consisting of hydrogen, hydrogen sulfide, hydrogen selenide, hydrogen telluride, carbon monoxide, ammonia, organic amine, silane, disilane, higher silanes, silylamines, diborane, hydrazine, methylhydrazine, chlorosilane and chloropolysilane, metal alkyl, arsine, phosphine, trialkylboron, oxygen, ozone, water, hydrogen peroxide, nitrous oxide, nitrogen monoxide, nitrogen dioxide, alcohols, plasma comprising fragments of those species, and combinations thereof, preferably ozone or water.

A method, wherein the temperature of the substrate is 100° C. to 700° C., preferably 150° C. to 450° C., and wherein the deposition chamber containing the substrate has a pressure of 1.33 Pa (=0.01 Torr) to 100 kPa (=800 Torr), preferably below 25 kPa (=200 Torr).

A method, further comprising the step of purging excess vapor comprising the at least one compound of formula (I) from the substrate, with an inert gas selected from the group consisting of hydrogen, nitrogen, helium, argon, and mixtures thereof.

A method, wherein the metal-containing layer has a thickness of more than 0 μm to 10 μm.

A method of manufacturing a semiconductor structure, comprising the steps of the method defined above, wherein the substrate is a semiconductor substrate.

Related Techniques for the Deposition of Vanadium (V) or Niobium (Nb) Containing Films The vaporization of the metal source is realized by introducing a carrier gas into a heated container containing the said metal source. The container is preferably heated at a temperature allowing to get the said metal source at a sufficient vapor pressure. The carrier gas can be selected from Ar, He, H$_2$, N$_2$ or mixtures of them. The said metal source can be mixed to a solvent or to another metal source or to a mixture of them in the container. The container can for instance be heated at temperatures in the range of 25° C.-200° C. Those skilled in the art will consider that the temperature of the container can be adjusted to control the amount of precursor vaporized. To control the evaporation level in the container, the pressure in the container can be modified. By reducing the pressure in the container, the level of vaporation of the metal source can be increased. The pressure in the container can for instance be changed in the range of mTorr till 800 Torr.

The said metal source can also be fed in liquid state to a vaporizer where it is vaporized. The said metal source can be mixed to a solvent. The said metal source can be mixed to another metal source. The said mixture of metal sources can be mixed to a solvent or a mixture of solvent. The said metal source can be mixed to a stabilizer. The said solvent can be selected in the group consisting of alcanes such as hexane, heptane, octane, aromatic solvents such as benzene, toluene, mesitylene, xylene, silicon containing solvent such as hexamethyldisiloxane, hexamethyldisilazane, tetramethylsilane, sulphur containing solvents such as dimethylsulfoxide, oxygen containing solvent such as tetrahydrofuran, dioxane.

The said vaporized metal source is then introduced into a reaction chamber where it is contacted to the surface of a substrate. The substrate can be heated to sufficient temperature to obtain the desired film at sufficient growth rate and with desired physical state and composition. Typical temperatures range from 100° C. to 700° C. Preferably the temperature is lower or equal to 450° C. The process can be assisted by a plasma technique, chosen without limitation, to improve the reactivity of the said vaporized metal source and/or the reactivity of other gaseous species, used in the process.

In one embodiment, the process of the invention consists in introducing simultaneously a Vanadium (V) or Niobium (Nb) metal-organic precursor described by the general formula $Cp(R^1)_mM(NR^2{}_2)_2(=NR^3)$ into a reaction chamber with or without a reagent. The said metal-organic precursor reacts by thermal self-decomposition with the surface of a substrate. The reagent is selected from reducing reactants, nitriding reactants, oxidizing reactants, or a mixture of them.

In one embodiment, the process of the invention consists in introducing simultaneously a Vanadium (V) or Niobium (Nb) metal-organic precursor described by the general formula $Cp(R^1)_mM(NR^2{}_2)_2(=NR^3)$ into a reaction chamber with or without a reagent and another metal source, being independently selected from any other element in the group II, III-A, III-B, Sulfur (S), tantalum (Ta), transition metal, lanthanoids, or rare-earth metals. The said metal-organic precursors react by thermal self-decomposition with the surface of a substrate. The reagent is selected from reducing reactants, nitriding reactants, oxidizing reactants, or a mixture of them.

In one embodiment, the process of the invention consists in introducing alternatively a Vanadium (V) or Niobium (Nb) metal-organic precursor described by the general formula $Cp(R^1)_mM(NR^2{}_2)_2(=NR^3)$ into a reaction chamber with a reagent. In a temperature range, the said metal-organic precursor reacts in a self-limited manner with the bonds present onto the surface of a substrate. Preferably, un-deposited metal-organic precursors molecules are removed from the reaction chamber. The reagent introduced, reacts also in a self-limited manner. Once all the complexes present on the surface of the substrate have reacted with the reagent, species are removed from the reaction chamber by a purge gas. The purge gas can for instance be selected within $N_2$, Ar, He, $H_2$ or mixtures of them. The purge gas may additionally contain other gas species that do not modify the chemical reactivity of the surface. Alternatively, the purge can be realized by vacuum. This process can be repeated as many times as necessary to reach the desired film thickness. The reagent is selected from reducing reactants, nitriding reactants, oxidizing reactants, or a mixture of them.

In one embodiment, the process of the invention consists in introducing alternatively first a Vanadium (V) or Niobium (Nb) metal-organic precursor described by the general formula $Cp(R^1)_mM(NR^2{}_2)_2(=NR^3)$ into a reaction chamber and second a reagent or another metal source, being independently selected from any other element in the group II, III-A, III-B, Sulphur (S), tantalum (Ta), transition metal, lanthanoids, or rare-earth metals. In a temperature range, the said metal-organic precursors react in a self-limited manner with the bonds present onto the surface of a substrate. Preferably, un-deposited metal-organic precursors molecules are removed from the reaction chamber. The reagent introduced, reacts also in a self-limited manner. Once all the complexes present on the surface of the substrate have reacted with the reagent, species are removed from the reaction chamber by a purge gas. The purge gas can for instance be selected within $N_2$, Ar, He, $H_2$ or mixtures of them. The purge gas may additionally contain other gas species that do not modify the chemical reactivity of the surface. Alternatively, the purge can be realized by vacuum. This process can be repeated as many times as necessary to reach the desired film thickness. The reagent is selected from reducing reactants, nitriding reactants, oxidizing reactants, or a mixture of them.

The compounds of the formula (I) or in admixture, are used to deposite films of various compositions (as disclosed herein after) using any well-known deposition method using vapor phase deposition, such as MOCVD (Metal Organic Chemical Vapor Deposition), ALD (Atomic Layer Deposition), PE-ALD (Plasma Enhanced Atomic Layer Deposition) and any other deposition method such as PECVD (Plasma Enhanced Chemical Vapor Deposition) or as pulsed CVD.

These new group V metal precursors are thus useful for pure metal, metallic oxide, oxynitride, nitride and/or silicide film deposition to make electrodes and/or high k layers, and/or copper diffusion barrier layers and the like.

In the ALD process the preferred temperature is in the range of 100° C. to 450° C., more preferably 150° C. to 350° C., the preferred pulse duration in ALD is one second, the preferred pressure is in the range of 0.01 Torr to 800 Torr, more preferably from 0.1 Torr to 200 Torr. and the preferred carrier gas is selected from $N_2$, He, Ar, $H_2$, more preferably Ar or $N_2$. The preferred $N_2$ canister flow is in the 30-200 sccm range, preferably 50 sccm to 100 sccm In the CVD process, the preferred temperature is in the range of 100° C. to 700° C., more preferably from 200° C. to 500° C., the preferred pressure is in the range of 0.01 Torr to 800 Torr, preferably from 1 Torr to 200 Torr and the preferred carrier gas is selected from $N_2$, He, Ar, $H_2$, more preferably Ar or $N_2$. The preferred $N_2$ canister flow is in the 30-200 sccm range, preferably 50 sccm to 100 sccm. In the PECVD process, the preferred temperature is in the range of 100° C. to 700° C., more preferably from 100° C. to 500° C., the preferred pressure is in the range of 0.01 Torr to 800 Torr, preferably from 1 Torr to 200 Torr, the preferred carrier gas is selected from $N_2$, He, Ar, $H_2$, more preferably Ar or $N_2$ and the preferred $N_2$ canister flow is in the 30-200 sccm range, preferably 50 sccm to 100 sccm. H or NH radicals are produced by a remote plasma system and used as co-reactant.

In these above mentioned uses, any of the compound of the formula (I) as defined above, can be used alone or in admixture with one or several other compounds of the said formula (I) and/or with any appropriate additive which useful when depositing a metal containing film as provided hereafter. According to a particular embodiment the invention relates to a use as defined above of such an admixture having a melting point lower than or equal to about 50° C. and more preferably lower than or equal to 35° C., i.e. shall be in liquid form or close to liquid form at room temperature, which makes their delivery easier, and or having a vapor pressure higher than 0.01 Torr at 100° C.

Various films can be obtained on a substrate by using the precursors described here above, such as nitrides, carbides, silicides, nitro-silicides (MSiN), oxydes (e.g. $MeO_j$), oxynitrides ($MO_xN_y$) and oxynitrides from two different metals $M^1$ and $M^2$ ($M^1M^2O_xN_y$).

The process according to the invention may be summarized as follows:

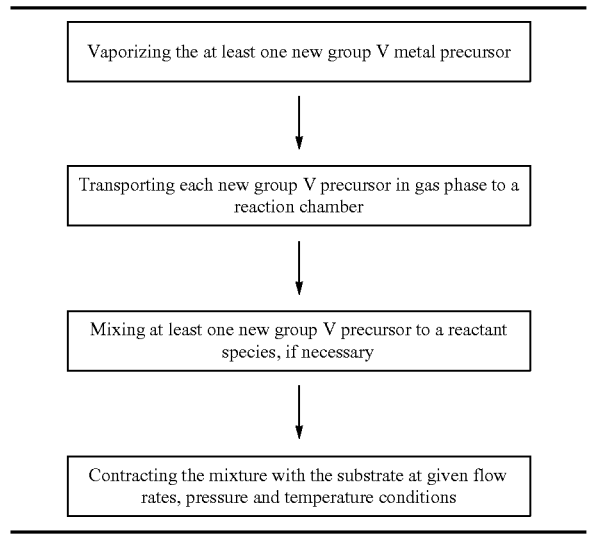

In accordance with one embodiment, the vaporization of the new metal source is realized by introducing a carrier gas into a heated container containing the said new metal source. The container is preferably heated at a temperature allowing to get the said metal source at a sufficient vapor pressure. The carrier gas can be selected, without limitation, from Ar, He, $H_2$, $N_2$ or mixtures of them. The said metal source can be mixed to a solvent or to another metal source or to a mixture of them in the container. The container can for instance be heated at temperatures in the range of 80° C.-140° C. Those skilled in the art will consider that the temperature of the container can be adjusted to control the amount of precursor vaporized.

In accordance with another embodiment, the said metal source is fed in liquid state to a vaporizer where it is vaporized. The said metal source can be mixed to a solvent. The said metal source can be mixed to another metal source. The said mixture of metal sources can be mixed to a solvent or a mixture of solvent. The said metal source can be mixed to a stabilizer.

The vaporized metal source is there after introduced into a reaction chamber where it is contacted to a substrate. The substrate can be heated to a sufficient temperature to obtain the desired film at sufficient growth rate and with desired physical state and composition. Typical temperature range from 100° C. to 700° C. Preferably the temperature is lower or equal to 450° C. The pressure in the reaction chamber is controlled to obtain the desired metal containing film at sufficient growth rate. Typical pressure range from 1.33 Pa (=0.01 Torr) to 13.3 kPa (=100 Torr) or higher.

According to another embodiment, it is possible to mix the metal source to a reactant species prior to the introduction of the mixture into the reaction chamber.

In another embodiment of the invention, the metal source may be mixed to a reactant species in the reaction chamber.

According to a further embodiment, the metal source and the reactant species are introduced simultaneously (chemical vapor deposition), sequentially (atomic layer deposition) or any combination thereof (one example is to introduce the metal source and the other metal source together in one pulse and oxygen in a separate pulse [modified atomic layer deposition]; another example is to introduce oxygen continuously and to introduce the metal sources by pulse (pulsed-chemical vapor deposition)).

It is also possible to introduce the reactant species into a plasma system localized remotely from the reaction chamber to decompose these species into radicals before their introduction into the reaction chamber.

According to a further embodiment, wherein the targeted metal based film contains oxygen, such as for example, without limitation metal, oxide or metal oxy-nitride, the reactant species shall include an oxygen source which is selected from the group comprising oxygen ($O_2$), oxygen radicals (for instance O or OH), for instance generated by a remote plasma, ozone ($O_3$), NO, $N_2O$, $NO_2$, moisture ($H_2O$) and $H_2O_2$ or any mixture thereof;

According to still a further embodiment, wherein the targeted metal based film contains nitrogen, such as for example metal nitride or metal carbo-nitride, the reactant species include a nitrogen source which is selected from, but not limited to, nitrogen ($N_2$), ammonia, hydrazine and alkyl derivatives, N-containing radicals (for instance N, NH, $NH_2$), NO, $N_2O$, $NO_2$, amines.

If the targeted metal based film contains carbon, such as for example without limitation metal carbide or metal carbo-nitride, the reactant species include a carbon source which is selected from, but not limited to, methane, ethane, propane, butane, ethylene, propylene, t-butylene, isobutylene, $CCl_4$.

If the targeted metal based film contains silicon, such as for example metal silicide, silico-nitride, silicate, silico-carbo-nitride, the reactant species shall include a silicon source which is selected from the group comprising $SiH_4$, $Si_2H_6$, $Si_3H_8$, TriDMAS, BDMAS, BDEAS, TDEAS, TDMAS, TEMAS, $(SiH_3)_3N$, $(SiH_3)_2O$, trisilylamine, disiloxane, trisilylamine, disilane, trisilane, a alkoxysilane $SiH_x(OR^1)_{4-x}$, a silanol $Si(OH)_x(OR^1)_{4-x}$ (preferably $Si(OH)(OR^1)_3$; more preferably $Si(OH)(OtBu)_3$ an aminosilane $SiH_x(NR^1R^2)_{4-x}$ (where x is comprised between 0 and 4; $R^1$ and $R^2$ are independently H or a C1-C6 carbon chain, either linear, branched or cyclic; preferably TriDMAS $SiH(NMe_2)_3$, BTBAS $SiH_2(NHtBu)_2$); BDEAS $SiH_2(NEt_2)_2$) and mixtures thereof. The targeted film can alternatively contain Germanium. The above-mentioned Si containing sources, may be replaced by similar Ge containing sources.

It is quite possible to mix a metal source to another metal source to deposit a multi-metal containing film, prior to their introduction into the reaction chamber or to simultaneously introduce into the reaction chamber, these metal sources and mix them together and/or with other reactant species in the reaction chamber.

But it is also possible to introduce the first metal source, the second metal source and the reactant species in the reaction chamber simultaneously (chemical vapor deposition), sequentially (atomic layer deposition) or any combination thereof (one example is to introduce the first metal source and the second metal sources together in one pulse and oxygen in a separate pulse [modified atomic layer deposition]; another example is to introduce oxygen continuously and to introduce the metal source by pulse (pulsed-chemical vapor deposition)).

The second metal source shall be selected from the group comprising tantalum, lanthanide and rare-earth metal source (Sc, Y, La, Ce, Pr, Nd, Gd . . . ) source such as rare earth diketonates $Ln(-O-C(R^1)-C(R^2)-C(R^3)-O-)(-O-C(R^4)-C(R^5)-C(R^6)-O-)(-O-C(R^7)-C(R^8)-C(R^9)-O-)$ (where each $R^i$ is independently H or a C1-C6 carbon chain, either linear, branched or cyclic), a cyclopentadienyl $Ln(R^1Cp)(R^2Cp)(R^3Cp)$ (where each $R^i$ is independently H or a C1-C6 carbon chain, either linear, branched or cyclic), $Ln(NR^1R^2)(NR^3R^4)(NR^5R^6)$ and mixtures thereof. The second metal source can alternatively be an aluminum source, selected from the group consisting of trimethyl aluminum, dimethyl aluminum hydride, an alkoxyalane $AlR^i_x(OR')_{3-x}$ (where x is comprised between 0 and 3; $R^1$ and $R^2$ are independently H or a C1-C6 carbon chain, either linear, branched or cyclic; preferably $AlR^1R^2(OR')$, most preferably $AlMe_2(OiPr)$), an amidoalane $AlR^i_x(NR'R'')_{3-x}$ (where x is comprised between 0 and 3; $R^1$ and $R^2$ are independently H or a C1-C6 carbon chain, either linear, branched or cyclic) and mixtures thereof. The other metal source can alternatively be a tungsten, molybdenum source. The other metal source can alternatively be a hafnium, zirconium or titanium source such as $M(OR^1)_4$ or other alkoxide-containing metal sources, $M(NR^1R^2)_4$, or adducts containing these species. The second metal source can alternatively be a divalent metal source (preferably Mg, Ca, Zn, Sr, Ba) selected from, but not limited to metal β-diketonates or adducts containing these species.

The reactants can be introduced simultaneously (chemical vapor deposition), sequentially (atomic layer deposition) any combination thereof.

EXAMPLES

1. CVD Process Using $NbCp(=NtBu)(NEtMe)_2$ and Ammonia $NbCp(=NtBu)(NEtMe)_2$ is stored into a container. The container is heated at 120° C. and $N_2$ is used as carrier gas at a flow of 50 sccm. Ammonia ($NH_3$) is used as nitrogen source. The substrate is heated at 400° C. The precursor is simultaneously introduced into the reaction chamber with $NH_3$. A film of niobium nitride is obtained.

2. ALD Process Using $NbCp(=NtBu)(NEtMe)_2$ and Ammonia $NbCp(=NtBu)(NEtMe)_2$ is stored into a container. The container is heated at 120° C. and $N_2$ is used as carrier gas at a flow of 50 sccm. Ammonia ($NH_3$) is used as nitrogen source. The substrate is heated at 400° C. The precursor is sequentially introduced into the reaction chamber with $NH_3$: during the first step a pulse of $NbCp(=NtBu)(NEtMe)_2$ is introduced during 8 seconds, followed by a 13 seconds $N_2$ purge. A pulse of $NH_3$ is then introduced into the reaction chamber during 8 seconds, followed by a 13 seconds $N_2$ purge. The first step is then done again. 400 cycles are performed this way. A film of niobium nitride is obtained.

The precursors according to the present invention are suitable for producing very thin, uniform and conformal thin films in high aspect ratio structures with control of the thickness and composition at the atomic level. Those films are highly desirable for applications in the semiconductor industry either as for example:
  a. Copper diffusion barrier in BEOL applications
  b. CMOS metal gate
  c. Electrodes in Metal-Insulator-Metal structures
  d. High-k layer in Metal-Insulator-Metal structures
Examples: $NbN_x$, VNx, Nb, V, VOx, NbOx, TaNbN, $TaNbO_x$, $BiNbO_x$, $BiTaNbO_x$.

Despite the precursors look very suitable for applications in the semiconductor industry, it is not limited to this industry only. V and Nb containing layers can be used among other applications to increase wear resistance, catalytic applications, and sensors.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method for forming a metal-containing layer on a substrate, the method comprising the steps of:
   a) providing a vapor comprising at least one precursor compound selected from the group consisting of $(Cp)V(=NtBu)(NEt_2)_2$; $(Cp)V(=NtBu)(NMe_2)_2$; $(Cp)V(=NtBu)(NEtMe)_2$; $(Cp)V(=NiPr)(NEt_2)_2$; $(Cp)V(=NiPr)(NMe_2)_2$; $(Cp)V(=NiPr)(NEtMe)_2$; $(Cp)V(=NC_5H_{11})(NEt_2)_2$; $(Cp)V(=NC_5H_{11})(NMe_2)_2$; $(Cp)V(=NC_5H_{11})(NEtMe)_2$; $(Cp)Nb(=NtBu)(NEt_2)_2$; $(Cp)Nb(=NtBu)(NMe_2)_2$; $(Cp)Nb(=NtBu)(NEtMe)_2$; $(Cp)Nb(=NiPr)(NEt_2)_2$; $(Cp)Nb(=NiPr)(NMe_2)_2$; $(Cp)Nb(=NiPr)(NEtMe)_2$; $(Cp)Nb(=NC_5H_{11})(NEt_2)_2$; $(Cp)Nb(=NC_5H_{11})(NMe_2)_2$; and $(Cp)Nb(=NC_5H_{11})(NEtMe)_2$;
   b) providing at least one reaction gas selected from the group consisting of ozone and water; and
   c) reacting the vapor and the reaction gas with the substrate, according to a deposition process, to form the metal-containing layer on at least one surface of the substrate.

2. The method of claim 1, wherein the deposition process is an atomic layer deposition process.

3. The method of claim 1, wherein the deposition process is a chemical vapor deposition process.

4. The method of claim 1, further comprising the step:
   d) reacting the metal-containing layer obtained in step c) with a reagent selected from the group consisting of another metal source, reducing reactants, nitriding reactants, oxidizing reactants, and combinations thereof.

5. The method of claim 1, wherein the vapor provided in step a) further comprises at least one precursor compound containing a metal $M^2$, and the metal-containing layer formed in step c) contains two metals $M^1$ and $M^2$, wherein $M^1$ is Vanadium or Niobium.

6. The method of claim 1, wherein a temperature of the substrate is 100° C. to 700° C. and wherein the deposition chamber containing the substrate has a pressure of 1.33 Pa to 100 kPa.

7. The method of claim 6, wherein the temperature is 150° C. to 450° C. and the pressure is below 25 kPa.

8. The method of claim 1, further comprising the step of purging excess vapor comprising the at least one precursor compound from the substrate with an inert gas selected from the group consisting of hydrogen, nitrogen, helium, argon, and mixtures thereof.

9. A method of manufacturing a semiconductor structure, comprising the steps of:
   forming a metal-containing layer on the semiconductor substrate by:
   a) providing a vapor comprising at least one precursor compound selected from the group consisting of $(Cp)V(=NtBu)(NEt_2)_2$; $(Cp)V(=NtBu)(NMe_2)_2$; $(Cp)V(=NtBu)(NEtMe)_2$; $(Cp)V(=NiPr)(NEt_2)_2$; $(Cp)V(=NiPr)(NMe_2)_2$; $(Cp)V(=NiPr)(NEtMe)_2$; $(Cp)V(=NC_5H_{11})(NEt_2)_2$; $(Cp)V(=NC_5H_{11})(NMe_2)_2$; $(Cp)V(=NC_5H_{11})(NEtMe)_2$; $(Cp)Nb(=NtBu)(NEt_2)_2$; $(Cp)Nb(=NtBu)(NMe_2)_2$; $(Cp)Nb(=NtBu)(NEtMe)_2$; $(Cp)Nb(=NiPr)(NEt_2)_2$; $(Cp)Nb(=NiPr)(NMe_2)_2$; $(Cp)Nb(=NiPr)(NEtMe)_2$; $(Cp)Nb(=NC_5H_{11})(NEt_2)_2$; $(Cp)Nb(=NC_5H_{11})(NMe_2)_2$; and $(Cp)Nb(=NC_5H_{11})(NEtMe)_2$;
   b) providing at least one reaction gas selected from the group consisting of ozone and water; and c) reacting the vapor and the reaction gas with the semiconductor substrate, according to a deposition process, to form the metal-containing layer on at least one surface of the semiconductor substrate.

10. The method of claim 9, wherein the deposition process is an atomic layer deposition process.

11. The method of claim 9, wherein the deposition process is a chemical vapor deposition process.

12. The method of claim 9, further comprising the step:
   d) reacting the metal-containing layer obtained in step c) with a reagent selected from the group consisting of another metal source, reducing reactants, nitriding reactants, oxidizing reactants, and combinations thereof.

13. The method of claim 9, wherein the vapor provided in step a) further comprises at least one precursor compound containing a metal $M^2$, and the metal-containing layer formed in step c) contains two metals $M^1$ and $M^2$, wherein $M^1$ is Vanadium or Niobium.

14. The method of claim 9, further comprising the step of purging excess vapor comprising the at least one precursor compound from the substrate with an inert gas selected from the group consisting of hydrogen, nitrogen, helium, argon, and mixtures thereof.

15. A compound selected from the group consisting of:
$(Cp)V(=NtBu)(NEt_2)_2$
$(Cp)V(=NtBu)(NMe_2)_2$
$(Cp)V(=NtBu)(NEtMe)_2$
$(Cp)V(=NiPr)(NEt_2)_2$
$(Cp)V(=NiPr)(NMe_2)_2$
$(Cp)V(=NiPr)(NEtMe)_2$
$(Cp)V(=NC_5H_{11})(NEt_2)_2$
$(Cp)V(=NC_5H_{11})(NMe_2)_2$ and
$(Cp)V(=NC_5H_{11})(NEtMe)_2$.

16. A compound selected from the group consisting of:
$(Cp)Nb(=NiPr)(NEt_2)_2$
$(Cp)Nb(=NiPr)(NMe_2)_2$
$(Cp)Nb(=NiPr)(NEtMe)_2$
$(Cp)Nb(=NC_5H_{11})(NEt_2)_2$
$(Cp)Nb(=NC_5H_{11})(NMe_2)_2$ and
$(Cp)Nb(=NC_5H_{11})(NEtMe)_2$.

* * * * *

UNITED STATES PATENT AND TRADEMARK OFFICE
CERTIFICATE OF CORRECTION

PATENT NO. : 8,460,989 B2  
APPLICATION NO. : 13/123013  
DATED : June 11, 2013  
INVENTOR(S) : Nicolas Blasco et al.

It is certified that error appears in the above-identified patent and that said Letters Patent is hereby corrected as shown below:

Title Page, Item (73) Assignee:

Change "L'Air Liquide Societe Anonyme pour l'Etude et l'Exploitation des Procedes" to --L'Air Liquide Societe Anonyme pour l'Etude et l'Exploitation des Procedes Georges Claude--

Claims:

Claim 6, Column 10, Line 40, change "100° C. to 700° C." to --100° C to 700° C--

Claim 7, Column 10, Lines 43-44, change "150° C. to 450° C." to --150° C to 450° C--

Signed and Sealed this  
Eighth Day of October, 2013

Teresa Stanek Rea  
*Deputy Director of the United States Patent and Trademark Office*